United States Patent
Poole et al.

(10) Patent No.: US 10,465,090 B2
(45) Date of Patent: Nov. 5, 2019

(54) POWDER COATING COMPOSITIONS WITH A POLYMERIC AROMATIC PRODUCT OF AN AROMATIC ISOCYANATE MANUFACTURING PROCESS

(71) Applicant: Covestro LLC, Pittsburgh, PA (US)

(72) Inventors: James Poole, Coon Rapids, MN (US); George Pavlovich, Pittsburgh, PA (US); Don S. Wardius, Pittsburgh, PA (US)

(73) Assignee: COVESTRO LLC, Pittsburgh, PA (US)

( * ) Notice: Subject to any disclaimer, the term of this patent is extended or adjusted under 35 U.S.C. 154(b) by 187 days.

(21) Appl. No.: 15/630,202

(22) Filed: Jun. 22, 2017

(65) Prior Publication Data
US 2018/0371287 A1 Dec. 27, 2018

(51) Int. Cl.

| | | |
|---|---|---|
| B32B 15/09 | (2006.01) | |
| B32B 15/08 | (2006.01) | |
| B32B 27/36 | (2006.01) | |
| C09D 5/03 | (2006.01) | |
| C09D 167/00 | (2006.01) | |
| C08G 63/02 | (2006.01) | |
| C08G 18/72 | (2006.01) | |
| C08L 63/06 | (2006.01) | |
| C08K 3/34 | (2006.01) | |
| C08K 3/26 | (2006.01) | |
| C07C 265/14 | (2006.01) | |
| C07C 265/12 | (2006.01) | |
| C09D 7/40 | (2018.01) | |
| C08G 18/79 | (2006.01) | |
| C08G 18/42 | (2006.01) | |
| C09D 7/61 | (2018.01) | |
| C09D 7/65 | (2018.01) | |
| C08K 3/30 | (2006.01) | |
| C08K 3/22 | (2006.01) | |

(52) U.S. Cl.
CPC .......... *C09D 167/00* (2013.01); *C07C 265/12* (2013.01); *C07C 265/14* (2013.01); *C08G 18/42* (2013.01); *C08G 18/727* (2013.01); *C08G 18/798* (2013.01); *C08G 63/02* (2013.01); *C08K 3/26* (2013.01); *C08K 3/34* (2013.01); *C08L 63/06* (2013.01); *C09D 5/03* (2013.01); *C09D 7/61* (2018.01); *C09D 7/65* (2018.01); *C09D 7/69* (2018.01); *C08G 2150/20* (2013.01); *C08K 2003/2227* (2013.01); *C08K 2003/265* (2013.01); *C08K 2003/267* (2013.01); *C08K 2003/3045* (2013.01); *C08L 2203/18* (2013.01); *C08L 2666/30* (2013.01)

(58) Field of Classification Search
None
See application file for complete search history.

(56) References Cited

U.S. PATENT DOCUMENTS

| | | | |
|---|---|---|---|
| 3,506,598 A * | 4/1970 | Groff | B05D 3/0218 |
| | | | 502/170 |
| 3,988,288 A | 10/1976 | Yamauchi et al. | |
| 4,093,674 A | 6/1978 | Tsutsui et al. | |
| 4,143,008 A | 3/1979 | Zwolinski et al. | |
| 4,151,220 A | 4/1979 | Watanabe et al. | |
| 4,165,406 A | 8/1979 | Tugukuni et al. | |
| 4,211,691 A | 7/1980 | Fitzgerald et al. | |
| 4,293,456 A | 10/1981 | Reischl | |
| 4,297,456 A | 10/1981 | Reischl et al. | |
| 4,311,800 A | 1/1982 | Reischl | |
| 4,424,313 A | 1/1984 | Meyer et al. | |
| 4,480,081 A | 10/1984 | Rosin et al. | |
| 5,229,460 A | 7/1993 | Yousuf et al. | |
| 5,334,631 A | 8/1994 | Durand | |
| 5,349,082 A | 9/1994 | Slack et al. | |
| 5,401,825 A * | 3/1995 | Kurz | C08G 18/678 |
| | | | 525/123 |
| 5,446,196 A | 8/1995 | Benedix et al. | |
| 5,786,419 A | 7/1998 | Meier-Westhues et al. | |
| 5,811,190 A | 9/1998 | Laas et al. | |
| 5,907,006 A | 5/1999 | Rennie et al. | |
| 6,034,178 A | 3/2000 | Decker et al. | |
| 6,111,017 A | 8/2000 | Imashiro et al. | |
| 6,737,467 B1 | 5/2004 | Decker et al. | |
| 6,858,257 B1 | 2/2005 | Cordiner | |
| 7,148,295 B2 | 12/2006 | Laas et al. | |
| 7,767,778 B2 | 8/2010 | Rawlins et al. | |
| 8,790,755 B2 | 7/2014 | Murai et al. | |
| 2012/0123062 A1 | 5/2012 | Laufer et al. | |
| 2013/0122765 A1 | 5/2013 | Ambrose et al. | |
| 2018/0371263 A1* | 12/2018 | Pavlovich | C09D 5/03 |

FOREIGN PATENT DOCUMENTS

| | | | | |
|---|---|---|---|---|
| CN | 105238268 A * | 1/2016 | | C09D 195/00 |
| EP | 0010675 A2 | 5/1980 | | |
| EP | 0767188 A1 | 4/1997 | | |
| EP | 0881243 A1 | 12/1998 | | |
| JP | 50018014 B * | 6/1975 | | C09D 3/24 |

(Continued)

OTHER PUBLICATIONS

Machine translation of JP-50018014-B (no date).*

(Continued)

*Primary Examiner* — Michael J Feely

(74) *Attorney, Agent, or Firm* — Donald R. Palladino

(57) ABSTRACT

Disclosed are powder coating compositions that include a polymeric aromatic product of an aromatic isocyanate manufacturing process.

22 Claims, No Drawings

(56) References Cited

FOREIGN PATENT DOCUMENTS

RU          1825811  A1 *  7/1993  ........... C09D 167/02
WO       2007075777  A2     7/2007

OTHER PUBLICATIONS

Translation of JP-50018014-B (no date).*
Machine translation of CN-105238268-A (no date).*
Singh et al; "Use of Isocyanate Production Waste in the Preparation of Improved Waterproofing Bitumen"; Journal of Applied Polymer Science; vol. 90; pp. 1365-1377 (2003); Wiley Periodicals, Inc.; Central Building Research Institute, Roorkee-247667, India.

* cited by examiner

POWDER COATING COMPOSITIONS WITH A POLYMERIC AROMATIC PRODUCT OF AN AROMATIC ISOCYANATE MANUFACTURING PROCESS

FIELD

The present invention relates generally to powder coating compositions that include a polymeric aromatic product of an aromatic isocyanate manufacturing process.

BACKGROUND

Powder coating typically involves applying a composition that is in the form of solid particulates to a substrate, which is often then subjected to heat for curing. The heating process melts the particulate resin components and results in a continuous coating film. Such coatings are often used as a decorative and/or protective coating on appliances, automotive parts, electrical/mechanical equipment, furniture, among many other articles. In some cases, powder coating compositions are used to provide corrosion-resistant coatings, such as in subsurface pipeline applications.

Powder coatings have gained widespread use due to their durability over the product life cycle, economic benefits and safety/environmental advantages. For example, powder coating compositions do not include volatile organic solvents that are often used in liquid coating compositions, which is environmentally desirable. Also, powder coating application typically takes place in a controlled plant environment using electrostatic spray equipment in enclosed areas, which promotes adhesion and enables collection of overspray material for reuse, thereby limiting waste materials.

Most powder coating compositions include fillers or extenders that can constitute up to 40% by weight of a typical thermosetting powder coating formulation. Extenders are typically a very inexpensive ingredient in the composition that is used to extend the capabilities of the resin and coloring pigment(s) in the composition. They often are chemically inert in the composition and have little or no hiding power. Examples of commonly used extenders are talc, silicon dioxide, barium sulfate, calcium carbonate, wollastonite, calcium silicate, magnesium carbonate, micronized dolomite, and aluminum oxide.

Such extenders are known to have a detrimental effect on certain properties of powder coatings, particularly if used in too great an amount. For example, the smoothness, consistency and/or gloss level of the coating may be adversely affected. Also, the specific gravity of a powder coating composition can affect the coverage ability of the composition, with lower specific gravities resulting in higher film coverage on a square foot/pound coating/mil basis. Typical inorganic extenders have a relatively high specific gravity, resulting in limitations in terms of coverage.

In subsurface applications in particular, such as pipeline coating applications, it is important that the cured coating be resistant to a loss of adhesion to the substrate, which is sometimes referred to as "disbondment" of the coating material. This disbondment can be exacerbated by the use of cathodic protection that is commonly applied to buried pipes. Therefore, resistance to cathodic disbondment is an important property for pipeline coatings, especially those that consistently operate at elevated temperatures. If the coating fails to adequately adhere to the pipe, the corrosion-resistance properties of the coated substrate are lost.

As a result, it would be desirable to provide powder coating compositions that include an extender that, unlike conventional inorganic extenders, is an organic material with functional properties not normally found in inorganic extenders. Moreover, because they are often used in applications in which protection against metal corrosion is important, it would be desirable to provide such powder coating compositions that result in cured coatings with good corrosion resistance properties and which are resistant to cathodic disbondment.

The present invention was made in view of the foregoing.

SUMMARY OF THE INVENTION

In certain respects, the present invention is directed to powder coating compositions. These powder coating compositions comprise: (a) a particulate film-forming resin; and (b) an organic particulate, different from (a), comprising: (i) a crosslinked polymer comprising aromatic groups, biuret groups, urea groups, and carbodiimide groups; and (ii) a high-boiling hydrocarbon.

The present invention is also directed to, among other things, related methods for coating a substrate, coated substrates and coated articles.

DETAILED DESCRIPTION

Various embodiments are described and illustrated in this specification to provide an overall understanding of the structure, function, properties, and use of the disclosed inventions. It is understood that the various embodiments described and illustrated in this specification are non-limiting and non-exhaustive. Thus, the invention is not limited by the description of the various non-limiting and non-exhaustive embodiments disclosed in this specification. The features and characteristics described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant(s) reserve the right to amend the claims to affirmatively disclaim features or characteristics that may be present in the prior art. Therefore, any such amendments comply with the requirements of 35 U.S.C. § 112 and 35 U.S.C. § 132(a). The various embodiments disclosed and described in this specification can comprise, consist of, or consist essentially of the features and characteristics as variously described herein.

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicant(s) reserves the right to amend this specification to expressly recite any subject matter, or portion thereof, incorporated by reference herein.

In this specification, other than where otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described in the present description should at least be construed in light of the number of reported significant digits and by applying ordinary rounding techniques.

Also, any numerical range recited in this specification is intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicant(s) reserves the right to amend this specification, including the claims, to expressly recite any sub-range subsumed within the ranges expressly recited herein. All such ranges are intended to be inherently described in this specification such that amending to expressly recite any such sub-ranges would comply with the requirements of 35 U.S.C. § 112 and 35 U.S.C. § 132(a).

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise.

As indicated, certain embodiments of the present invention are directed to powder coating compositions. As used herein, the term "powder coating composition" refers to coating compositions that are in the form of solid particulates, as opposed to coating compositions that are in a liquid form. Such particulates may have a small particle size (less than 10 micron) or may be of larger particle sizes. In certain embodiments, the powder coating compositions of the present invention are in the form of solid particulates having a particle size from 0.3 to 300 microns, such as 1 to 100 microns.

The powder coating compositions of the present invention comprise a film-forming resin. As used herein, the term "film-forming resin" refers to resins that can form a self-supporting continuous film on at least a horizontal surface of a substrate upon curing of the resin. In certain embodiments, the film-forming resin cures upon reaction of functional groups on the resin with a curing agent, i.e., the film-forming resin comprises a thermosetting film-forming resin, as will be understood by those skilled in the art.

Thermosetting film-forming resins that are suitable for use in the powder coating compositions of the present invention include, but are not limited to, carboxylic acid functional resins, such as polyester and acrylic resins, epoxy-functional resins, epoxy-polyester hybrid resins, hydroxyl functional resins, such as acrylic resins and polyester resins, fluorine-containing resins, alkyd resins, phenolic resins, melamine resins, urea resins, silicone resins, and amide resins.

Suitable carboxylic acid polyester resins include those described in U.S. Pat. Nos. 7,767,778, 5,811,190, 5,786,419, and 4,424,313 and include resins sold under the commercial names of Rucote, Crylcoat, Uralac, ReaFree, Sparkle, Albester, and Polymac. Suitable epoxy functional resins include those described in U.S. Pat. No. 7,148,295 and also include resins sold under the names of Kukdo, Araldite, Epon, and DER. Suitable acrylic resins include those described in U.S. Pat. No. 4,093,674 and also sold under the names of Joncryl (Sun Polymers). Suitable hydroxyl polyester resins include those described in U.S. Pat. No. 6,737,467 and also sold under the names of Rucote, Crylcoat, Uralac, ReaFree, Sparkle, Albester, and Polymac. Suitable fluoro resins include those described in U.S. Pat. No. 5,229,460 and also sold under the names of Lumiflon and Kynar. Suitable alkyd resins include those described in U.S. Pat. Nos. 3,988,288, 4,165,406, 4,211,691 and also sold under the name of Synray. Suitable phenolic resins include those described in U.S. Pat. No. 5,334,631 and also sold under the names of Bakelite, Durez, and Plyophen. Suitable melamine resins include those described in U.S. Pat. No. 4,151,220 and also sold under the names of Cymel, Sadview, and Astro. Suitable urea resins include those described in U.S. Pat. Nos. 6,858,257, 4,151,220 and also sold under the names of Urecoll and Synpol. Suitable silicone resins include those described in U.S. Pat. No. 6,034,178 and also sold under the names of Silres (Dow Corning). Suitable amide resins include those described in U.S. Pat. No. 5,907,006 and also sold under the names of Nylon and Akulon.

In certain embodiments of the present invention, the thermosetting film-forming resin comprises an epoxy resin of the formula:

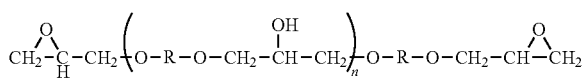

where n is a positive value, such as a number having an average value of 0.15 to 18 and R is an aromatic radical. In some embodiments, the epoxy resin is of a epichlorohydrin-bisphenol A type that has the foregoing formula in which R is an aromatic radical of the formula:

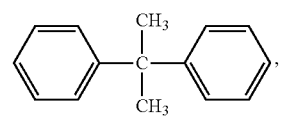

where n is sufficiently large to provide a resin having a Gardner-Holdt viscosity measured at 25° C. at 40% solids in diethylene glycol monobutyl ether of 50-150 and an epoxide equivalent weight of 400-750. The epoxide equivalent weight is the weight in grams of resin that contains one equivalent of epoxide.

In certain embodiments of the present invention, the curing agent comprises triglycidyl isocyanurate ("TGIC"), as a curing agent for carboxylic acid functional resins.

In certain embodiments of the present invention, the curing agent comprises, as a curing agent for epoxy-functional resins, a diamine, such as an aliphatic diamine, aromatic diamine and/or a heterocyclic diamine, an acid anhydride, a dihydrazide, a dicyandiamide, a polyamide resin obtained by the reaction of diamine with aliphatic acids and their dimers, acid anhydrides, a thiol, and/or a phenol. In some of these embodiments, the curing agent comprises an accelerated dicyandiamide having addition reactivity and self-polyaddition catalytic activity between epoxy groups, the derivatives thereof, and imidazoles.

Other suitable curing agents include, but are not limited to, polyfunctional acids for epoxy reactive group containing film-forming resins. Suitable curing agents for hydroxyl functional resins include, but are not limited to, blocked isocyanates, such as those of the type of the mentioned in the Examples.

In certain embodiments, the film-forming resin is present in the powder coating composition in an amount of 50 to 90, such as 50 to 70, % by weight, based on the total weight of the powder coating composition. In certain embodiments, the curing agent, when used, is present in an amount of 1 to 10, such as 2 to 6, % by weight, based on the total weight of the powder coating composition.

As indicated earlier, the powder coating compositions of the present invention comprise an organic particulate, different from (a), comprising: (i) a crosslinked polymer comprising aromatic groups, biuret groups, urea groups, and carbodiimide groups; and (ii) a high-boiling hydrocarbon. As used herein with reference to component (i) above, the term "polymer" encompasses oligomers and both homopolymers and copolymers; the prefix "poly" referring to two or more. Also, as used herein with reference to component (i) above, "crosslinked polymer" means that the chains of the polymer are linked to one another by covalent bonds so that the polymer, as a network, is insoluble in inert organic solvents and cannot be melted without decomposing.

The organic particulate (b) that is included in the powder coating compositions of the present invention is, in certain embodiments, the by-product of a process used to manufacture an aromatic polyisocyanate. More particularly, in certain embodiments, the organic particulate (b) is produced by drying a mixture comprising: (i) a residue, i.e., a by-product, of a process for producing an aromatic polyisocyanate by the reaction of a corresponding amine with phosgene; and (ii) a high-boiling hydrocarbon. As used herein, the term "high-boiling hydrocarbon" encompasses pure hydrocarbons and industrial mixtures that have a boiling point which is different from the boiling point of the polyisocyanate produced by the process resulting in the residue by at least 150° C. at 15 mbar.

For example, in some embodiments, the organic particulate is the product of a process for the production of a pure, distilled aromatic polyisocyanate by (1) the reaction of the corresponding amine with phosgene in a suitable solvent and multi-stage distillative work-up of the isocyanate solution obtained to recover pure isocyanate, pure solvent and an isocyanate-containing residue, and (2) continuously feeding the residue obtained from the distillation process and from 2 to 50 weight % of a high-boiling hydrocarbon which is inert under the distillation conditions to a heated, product-agitating vacuum drier with a horizontal shaft. In such a process, the fraction of polyisocyanate still present is continuously distilled off from the residue at a temperature of from 160° to 280° C. and a pressure of from 2 to 50 mbar. The remaining residue is continuously discharged as a pourable, non-dusting, granular material, which is cooled and ground to a desired particle size.

Residues from the synthesis of any of a variety of aromatic polyisocyanates are suitable for use in the present invention. Suitable such aromatic polyisocyanates include, but are not limited to, 1,3-Phenylene diisocyanate, 1,4-Phenylene diisocyanate, 2,6-toluene diisocyanate, 2,4-toluene diisocyanate, 1,3-Xylylene diisocyanate, 1,4-Xylylene diisocyanate, tetramethylxylene diisocyanate, 1,5-Naphthalene diisocyanate, Diphenyl oxide 4,4'-diisocyanate, 4,4'-Methylenediphenyl diisocyanate, 2,4'-Methylenediphenyl diisocyanate, 2,2'-Diisocyanatodiphenylmethane, Diphenylmethanediisocyanate, 3,3'-Dimethyl-4,4'-biphenylene isocyanate, 3,3'-Dimethoxy-4,4'-biphenylene diisocyanate, Benzene, 1-[(2,4-diisocyanatophenyl)methyl]-3-isocyanato-2-methyl, 2,4,6-triisopropyl-m-phenylene diisocyanate, and triphenylmethane-4,4',4"-triisocyanate, tris(p-isocyanatophenyl)thiophosphate, among others.

The residue stream, i.e., that chemical mixture containing the by-product, being formed during distillation of the amine/phosgene reaction mixture often contains from 20 to 80 weight %, such as 40 to 60 weight %, of monomeric isocyanate in addition to polymeric products. In the practice of the process described above, this isocyanate-containing residue may be fed to the drier separately from the hydrocarbons in a plurality of partial streams. In certain embodiments, at least a portion of the isocyanate-containing residue is mixed with the hydrocarbon and fed to the drier. The remainder of the residue may then be fed to the drier in one or more partial streams.

A continuously operating contact drier which has a double shell for heating, has a horizontal shaft which agitates the product and is heated is, in certain embodiments, used as the drier in the production of the organic particulate (b) used in the powder coating compositions of the present invention. In certain embodiments, the drier has a plurality of nozzles for product admission, one nozzle for product discharge, and vapor discharge nozzles of large dimensions for the isocyanate and solvent which are separated from the residue during the distillation. Both single-shaft driers and double-shaft or screw feed apparatuses may be used.

Condensate formed from vapors generated during the process (e.g., in a vapor offtake system) may be used to remove dust deposits such as those which may be formed on the walls of the apparatus at the point where vapors are removed from the system (e.g., the vapor offtake system). These condensates are often separately discharged.

In certain embodiments of the process for preparing the organic particulates (b) used in the powder coating compositions of the present invention, the reactor is operated at a temperature of from 160° C. to 280° C., such as 200° C. to 250° C., under a pressure of from 2 to 50 mbar, such as 10 to 20 mbar, at a throughput of up to 250 kg/hour per m² of heating surface. The continuous distillation is often conducted in a product-agitating drier with a horizontal shaft, to which a condensation system is attached. Distillation is carried out in the presence of one or more hydrocarbons, which are admixed in an amount of from 1 to 50 weight %, such as 3 to 10 weight %, based on the weight of the residue being treated. Suitable hydrocarbons include, but are not limited to, asphalts and bitumens, such as those which occur industrially as by-products in the refining of crude oil. Specific non-limiting examples of suitable bitumens are those of grades 6/12, 10/20, 20/30, 30/40, 40/50, 60/70, 80/100, 100/120, and 180/200.

Suitable processes and equipment for producing the organic particulates (b) suitable for use in the present invention are also described in U.S. Pat. No. 5,446,196, at col. 2, line 18 to col. 4, line 2, the cited portion of which being incorporated herein by reference.

In certain embodiments, for purposes of the present invention, the organic particulate (b) produced as described above is ground to a mean particle size of at least 0.1 micron, such as at least 1 micron, at least 2 microns, or, in some cases, at least 5 microns and no more than 100 microns, such as no more than 50 microns or no more than 20 microns. In certain embodiments, the organic particulate (b) has a Mohs hardness of 2 to 4, and/or a specific gravity of 1.2 to 1.4 and/or a refractive index of 1.43 to 1.45. Furthermore, in certain embodiments, the ash content of the particulate (b) is less than 0.5% by weight, and when heated under a nitrogen atmosphere the particulate (b) shows no discernable melting point. In certain embodiments, the particulate (b) is insoluble in water at room temperature and pressure, and has a solubility of less than 0.1% at room temperature/pressure in any of the following organic solvents: acetone, chlorobenzene, xylenes, dimethylformamide, dimethylsulfoxide, dimethylacetamide, 1:1 mixture of acetone:aromatic 100, carbon disulfide, chloroform, methylene chloride, or tetrahydrofuran. It is not possible to analyze the particulate (b) by SEC or NMR because of its insolubility in organic solvents.

In certain embodiments, the organic particulate (b) is present in the powder coating composition in an amount of at least 0.01%, such as at least 2%, at least 5%, at least 10%, or, in some cases, at least 15% weight and/or up to 20%, such as up to 25%, up to 30%, up to 35%, or, in some cases, up to 40% weight, based on the total weight of the powder coating composition.

In certain embodiments, the powder coating compositions of the present invention comprise a catalyst to increase the rate of reaction between a film-forming resin and a curing agent. Suitable such catalysts include, but are not limited to, tin compounds, onium compounds, such as ethyltriphenylphosphonium acetate, tetraphenylphosphonium iodide, tetraphenylphosphonium acetate-acetic acid complex, phenyltriethylphosponium bromide, tetrabutylammonium acetate, and tetrabutylphosphonium bromide, amines, imidazoles, cyclic amidine, alkyl/aryl ammonium halides, and zinc alkyl/aryl thiocarbamates. In certain embodiments, the catalyst is present in the coating composition in an amount of 0.5 to 10 percent by weight, such as 3 to 5 percent by weight, based on the total weight of the composition.

The powder coating compositions of the present invention may also comprise any of a variety of other optional ingredients, such as waxes for flow and wetting, flow control agents, degassing additives, antioxidants and UV light absorbers. In certain embodiments, the powder coating composition comprises any of various pigments, such as, but not limited to, titanium dioxide, in which such pigment(s) can be present in an amount of up to 80 percent of the weight of the entire coating composition.

In certain embodiments, the powder coating compositions of the present invention also comprise an inorganic extender, such as talc, silicon dioxide, barium sulfate, calcium carbonate, wollastonite, calcium silicate, magnesium carbonate, micronized dolomite, and aluminum oxide. In certain embodiments, the amount of such inorganic extender in the powder coating compositions of the present invention is such that the weight ratio of the organic particulate (b) to inorganic extender is at least 0.1:1, such as at least 0.3:1, at least 1:1, or at least 1.3:1 and, in some cases, no more than 10:1, no more than 7:1 or no more than 3:1.

The powder coating compositions of the present invention can be prepared, for example, by thoroughly mixing the components to enable spatial homogeneity of the ingredients. The composition may then be intimately melt kneaded in an extruder at, for example, extrusion zone temperatures of, for example, 40° C. to 125° C., such as 45° C. to 120° C. The exiting extrudate may then be rapidly cooled and the resulting chip can be micronized into powder with an average particle size of 0.1 to 300 microns, such as 1 to 100 microns by, for example, using an air-classifying mill, a roller mill, a jet attrition mill, an impact mill, and/or a ball mill. Additives to improve fluidization of the powder and/or improve the resistance to impact fusion may be incorporated into the final product before or after micronization.

The powder coating compositions of the present invention can be applied to a substrate by, for example, by electrostatic spraying in a single sweep or in several passes to provide a film having a thickness after cure of from 1 to 10 mils (25 to 250 microns), such as 2 to 4 mils (50 to 100 microns).

In certain embodiments, after application, the powder coating compositions of the present invention are cured by heating, such as at a temperature of 80° C. to 200° C., for, for example, 3 to 30 minutes. Heating can be accomplished by any suitable means, such as placing the coated substrate in an oven or using infrared radiation.

As a result, the present invention is further directed to methods for coating a substrate comprising applying to the substrate one or more of the coating compositions described above by electrostatic spraying and curing the coating composition. Suitable substrates include, without limitation, certain plastics, wood, and metal. In certain embodiments, the substrate is a pipeline that is buried in the ground or submerged in water.

It has been discovered, surprisingly, that certain powder coating compositions of the present invention can have improved performance properties, such as corrosion resistance, heat resistance, and/or improved coverage, relative to similar powder coatings compositions utilizing solely $BaSO_4$ as the extender. In addition, it has been discovered, surprisingly, that certain powder coating compositions of the present invention can have improved resistance to cathodic disbondment, relative to similar powder coatings compositions utilizing solely inorganic extenders, such as wollastonite. Examples of testing results are given below. Such coatings can embodied in a variety of colors, however, in some embodiments, due to the color of the organic extender described herein, are often embodied in earth tone colors, such as tan, beige, or brown.

In addition to the examples shown here, the initial experimentation which was carried out to investigate the feasibility to make a useful powder coating by employing the organic particulate of this invention examined a number of essential properties of any good powder coating, including uniformity of the coating, including of its thickness, the level of gloss as a function of the range of particle sizes and loading of the organic particulate, gel time, the glass transition temperature, the forward and reverse impact resistance, the MEK (solvent) resistance, and the PCI smoothness of the resulting powder coating. In general it was found that there is a broad latitude in which the organic particulate of this invention may be employed to make powder coatings which could be useful for industry.

EXAMPLES

Examples 1-4

Powder coating compositions were prepared using the ingredients and amounts (in parts by weight) listed in Table 1. All formulas for testing were processed on a 24 mm twin screw extruder after proper weighing and mixing. Formulas were weighed on a Monobloc Weighing Technology Scale calibrated to the nearest 0.1 gram. The dry mixture was physically mixed until a homogeneous mixture was obtained. The mixture was fed to the extruder wherein the Zone 1 temperature was 90° C. and Zone 2 temperature was 110° C. The screw speed on the extruder was 425 rpm. The feed rate was adjusted to obtain the appropriate torque of 80 to 100 Nm. The typical residence time of the material in the extruder was relatively short at about 0.5 minutes. Extrudate was cooled immediately by passing through a set of rollers. Extruder chip was ground and sifted thru a #140 screen (106 microns), which resulted in a powder coating composition.

TABLE 1

| Ingredients | Example 1 (Comparative) | Example 2 | Example 3 (Comparative) | Example 4 |
|---|---|---|---|---|
| Rucote ® 9010[1] | 558 | 558 | — | — |
| Rucote ® XP 1006[2] | — | — | 498 | 498 |
| Tepic ® G[3] | 42 | 42 | — | — |
| Crelan ® NI2[4] | — | — | 102 | 102 |
| Benzoin | 5 | 5 | 5 | 5 |
| Flow Agent[5] | 10 | 10 | 10 | 10 |
| Sactofine LG[6] | 375 | 225 | 375 | 225 |
| Organic particulate[7] | — | 150 | — | 150 |
| Carbon Black Pigment, Raven ® 1255[8] | 10 | 10 | | |
| Carbon Black Pigment, Raven ® 2500[8] | | | 10 | 10 |
| Total | 1000 | 1000 | 1000 | 1000 |

[1]A carboxylic acid functional polyester resin, acid value (mg KOH/g) = 36, OH number (mg KOH/g) = 4, viscosity (ICI cone and plate at 200° C./cPS) = 3800, glass transition temperature = 67° C., from Stepan Company
[2]A hydroxyl functional polyester resin, OH number (mg KOH/g) = 45, viscosity (ICI cone and plate at 200° C./cPS) = 2000, glass transition temperature >52° C., from Stepan Company
[3]Tris (2,3-Epoxy propyl) Isocyanurate, epoxy equivalent weight = 107, from Nissan Chemical America Corporation
[4]An IPDI uretdione derivative, commercially available from Covestro.
[5]Resiflow ® PL-200, a liquid acrylic polymer on silica type filler from Estron Chemical.
[6]A functional white barium sulfate from Sachtleben Chemie GmbH
[7]An organic particulate comprising: (i) a crosslinked polymer comprising aromatic groups, biuret groups, urea groups, and carbodiimide groups; and (ii) a high-boiling hydrocarbon, prepared according to the process described in U.S. Pat. No. 5,446,196, which was processed in an attrition mill to give a fine powder with average mean particle size of 10 microns.
[8]either Raven ® 1255 or 2500, as indicated, from Columbian Chemical Company Coated Substrates The powder coating compositions of Examples 1-4 were applied at 2-4 mils dry film thickness to panels (3 by 5 inches) made of phosphated carbon steel. The coated panels were then cured in an oven for 15 min at 400° F. (dwell time). The panels used were Q-Panels Stock # R-46-I, Bonderite 1000 iron Phosphate, P60 Cr, DI Rinse. The oven used was a Precision Scientific Electric Convection Oven Model 625.

Testing

Coated panels were subjected to accelerated weathering according to ASTM D4587 Cycle 2: UV-A. After exposure for various time periods, the panels were evaluated for gloss retention (at 60°) according to ASTM D523 and color difference according to ASTM D2244 using CIE L*a*b* color space. Panels were also evaluated by the humid salt fog exposure test by following ASTM B117, also for 1008 hours. Results are set forth in Table 2.

TABLE 2

Results from Accelerated Weathering and Humid Salt Fog Exposure Tests, 0 or 1008 hours

| | Example 1 (Comparative) | Example 2 | Example 3 (Comparative) | Example 4 |
|---|---|---|---|---|
| Zero hours, 60° Gloss | 49.7 | 44.8 | 47.1 | 42.9 |
| 1008-hours, 60° Gloss | 57 | 21.3 | 45.1 | 9.1 |
| 1008-hours, ΔE | 0.91 | 3.04 | 0.48 | 1.4 |
| 1008-hours, ΔL | 0.86 | 3.04 | 0.24 | 1.34 |
| 1008-hours, Δa | 0.11 | 0.15 | 0.13 | 0.14 |
| 1008-hours, Δb | −0.28 | −0.14 | −0.4 | −0.38 |
| 1008-hours, Rating from B117, humid salt fog exposure | 6 | 6 | 5 | 5 |

Comparing example 2 to comparative example 1 (TGIC crosslinker) it is clear that the use of Organic particulate did not compromise the results of the ASTM B117 salt fog exposure test, 1008 hours (evaluation of rust creepage for scribed specimens, ASTM D1654, method 1). Note: there was zero blistering in the unscribed area.

Comparing example 4 to comparative example 3 (uretidione crosslinker) it is clear that the use of Organic particulate did not compromise the results of the ASTM B117 salt fog exposure test, 1008 hours (evaluation of rust creepage for scribed specimens, ASTM D1654, method 1). Note: there was zero blistering in the unscribed area.

These examples demonstrate that either type of crosslinker, TGIC or uretidione, could be employed when using Organic particulate as a filler, and either of which resulted in a powder coating which performed satisfactorily in weathering and humid salt spray tests.

Examples 5-8

Having generally shown that either type of important cross-linker may be used to prepare the powder coatings of this invention, further experimental work was carried out to investigate the suitable levels of Organic particulate and to identify any property trade-offs that may result in varying the level of the Organic particulate in the powder coating formulation. Using the same procedures that were explained in examples 1-4, powder coating compositions were prepared using the ingredients and amounts (in parts by weight) listed in Table 3

TABLE 3

| | Composition | | | |
|---|---|---|---|---|
| Ingredients | Example 5 | Example 6 | Example 7 | Example 8 (Comparative) |
| Rucote ® 9006[1] | 558 | 558 | 558 | 558 |
| Tepic ® G[2] | 42 | 42 | 42 | 42 |
| Catalyst[3] | 7 | 7 | 7 | 7 |
| Flow Agent[4] | 8 | 8 | 8 | 8 |
| Outgassing Agent[5] | 5 | 5 | 5 | 5 |
| Sactofine LG[6] | 220 | 270 | 320 | 370 |

TABLE 3-continued

| | Composition | | | |
|---|---|---|---|---|
| Ingredients | Example 5 | Example 6 | Example 7 | Example 8 (Comparative) |
| Organic particulate[7] | 150 | 100 | 50 | 0 |
| Carbon Black Pigment[8] | 10 | 10 | 10 | 10 |
| Total | 1000 | 1000 | 1000 | 1000 |

[1]A carboxylic acid functional polyester resin, acid value (mg KOH/g) = 36, OH number (mg KOH/g) = 4, viscosity (ICI cone and plate at 200° C./cPS) = 3800, glass transition temperature = 67° C., from Stepan Company
[2]Tris (2,3-Epoxy propyl) Isocyanurate, epoxy equivalent weight = 107, from Nissan Chemical America Corporation
[3]A 5% active masterbatch of TPEPB (tetrabutylphosphonium bromide) in Rucote ® 9006.
[4]Resiflow ® PL-200, a liquid acrylic polymer on silica type filler from Estron Chemical.
[5]Powdermate ® 542DG, a polymer based surfactants with low melt viscosity, from Troy Chemical Company.
[6]A functional white barium sulfate from Sachtleben Chemie GmbH
[7]An organic particulate comprising: (i) a crosslinked polymer comprising aromatic groups, biuret groups, urea groups, and carbodiimide groups; and (ii) a high-boiling hydrocarbon, prepared according to the process described in U.S. Pat. No. 5,446,196, which was processed in an attrition mill to give a fine powder with an average mean particle size of 10 microns.
[8]Raven ® 1255, from Columbian Chemical.

Coated Substrates

The powder coating compositions of Examples 5-8 were applied at 2-4 mils dry film thickness to panels (3 by 5 inches) made of phosphated carbon steel. The coated panels were then cured in an oven for 15 min at 400° F. (dwell time). The panels used were Q-Panels Stock # R-46-I, Bonderite 1000 iron Phosphate, P60 Cr, DI Rinse. The oven used was a Precision Scientific Electric Convection Oven Model 625.

Testing

Coated panels were subjected to accelerated weathering according to ASTM D4587 Cycle 2: UV-A. After exposure for various time periods, the panels were evaluated for gloss retention (at 60°) according to ASTM D523 and color difference according to ASTM D2244 using CIE L*a*b* color space. Results are set forth in Tables 4 and 5.

TABLE 4

| UV A | % Initial Specular Gloss Retention | | | |
|---|---|---|---|---|
| exposure (hours) | Example 5 | Example 6 | Example 7 | Example 8 (Comparative) |
| 168 | 97 | 96 | 97 | 96 |
| 336 | 88 | 85 | 83 | 87 |
| 504 | 81 | 76 | 73 | 79 |
| 672 | 65 | 66 | 61 | 70 |
| 840 | 52 | 54 | 45 | 58 |

As is apparent, the inventive examples 5, 6, and 7 retained a generally similar level of gloss compared to the comparative example. These results were confirmed by visual inspection, where the difference in gloss retention amongst the panels is not discernible.

TABLE 5

| UV A | Delta E (Total Color Difference) | | | |
|---|---|---|---|---|
| exposure (hours) | Example 5 | Example 6 | Example 7 | Example 8 (Comparative) |
| 168 | 0.4 | 0.47 | 0.38 | 0.36 |
| 336 | 0.85 | 0.86 | 0.66 | 0.73 |
| 504 | 0.98 | 1.14 | 0.9 | 0.78 |
| 672 | 1.16 | 1.14 | 0.99 | 0.76 |

TABLE 5-continued

| UV A | Delta E (Total Color Difference) | | | |
|---|---|---|---|---|
| exposure (hours) | Example 5 | Example 6 | Example 7 | Example 8 (Comparative) |
| 840 | 1.53 | 1.59 | 1.63 | 1.12 |
| 1008 | 3.1 | 5.25 | 5.09 | 3.18 |

As is apparent, the color retention results for coated panels using the inventive formulations were similar to those of the comparative formulation.

Corrosion testing was performed on panels for resistance to the onset of corrosion, where the test panels were exposed to periodic salt spray and humidity. The "salt fog test" per ASTM B117 was used, and the test duration was 1008 hours. Corrosion onset was determined from visual measurements of a scribe mark, made before the panel was inserted into the salt fog chamber, according to ASTM D1654-08. The degree of overall corrosion was rated on a scale of 0 to 10, where 0=severe corrosion, and 10=no corrosion. Blistering tests were performed according to ASTM D714-02. Results are set forth in Table 6.

TABLE 6

| Location of Corrosion on Test Panel | Degree of Corrosion | | | |
|---|---|---|---|---|
| | Example 5 | Example 6 | Example 7 | Example 8 (Comparative) |
| Overall | 9 | 9 | 5 | 5 |
| Isolated | 7 (one spot) | 5 (one spot) | No spots | No spots |
| Blistering | 0 | 0 | 0 | 0 |

As shown in Table 6, panels coated with the powder coating compositions of Examples 5 and 6 performed better than the comparative example 8. This is best seen in the overall scores, the first row of the table, since Examples 5 & 6 scored "9" as compared to "5" for Example 7 and the comparative example 8. This implies that a minimum level of 100 parts of organic particulate was required to attain good performance in the "salt spray test" according to the formulations given in Table 3.

Cured panels produced from the powder coating compositions of Examples 5 and 6 were placed in a Precision Scientific Mechanical Electric oven set at a temperature of 425° F. (218.3° C.) for 4 hours for heat resistance testing. After exposure, Gloss retention (ASTM D523), Impact Resistance (ASTM D2794) and Chemical Resistance (PCI #8, Reagent A) were compared to original values prior to exposure. Results are in Table 5.

TABLE 7

| Properties Tested | Example 5 | Example 8 (Comparative) |
|---|---|---|
| Gloss retention | Adequate | less than adequate |
| Impact resistance | Good | fair |
| Chemical resistance | very good | fair |

As is apparent, panels coated with the powder coating composition of example 1 performed better than the comparative example. These results indicate that the powder coating compositions of the present invention may provide superior performance to objects subject to excessive heat, such as manufacturing equipment, automobile parts, steel mill equipment such as motor housings and other machinery parts.

Since the Organic particulate (b) described above is an organic material that is relatively low in specific gravity (sp. gr.=1.2 to 1.4) as determined by comparison to distilled water) as compared to the inorganic extenders it can replace (sp. gr. of $BaSO_4$=4.4), powder coating formulations employing such particulates are believed to have a greater coverage per unit weight of formulated product at a given film thickness. This is because the higher the specific gravity of a powder coating composition, the more powder by weight will be needed to cover a given area. The advantages of lower specific gravity can be seen in the following equation, where a powder coating composition with a specific gravity of 1.0 yields a 1 mil thick coating for an area of 193.2 $ft^2$, assuming a theoretical transfer efficiency of 1.0 (100%).

Powder Coverage($ft^2$)=(193.2/sp.gr.)×Transfer Efficiency/$S_g$

In which the variable, $S_g$, in the equation for Powder Coverage stands for the specific gravity of the powder coating composition. For example, the specific gravity of the powder coating composition of Comparative Example 8 was calculated to be 1.64 and the specific gravity of the powder coating composition of Example 5 was calculated as 1.38. Using the formula above for a 1 mil thick coating and assuming a transfer efficiency of 100%, the film coverage for the powder coating composition of Comparative Example 8 was calculated to be 118 $ft^2$ (11 $m^2$) and the film coverage for the powder coating composition of Example 5 was calculated to be 140 ft (13 $m^2$), a 19% increase.

The flexibility, adhesion, impact resistance, solvent cure and pencil hardness of coatings produced from the powder coating composition of Examples 5-8 was also evaluated. The results are in Table 8. As is apparent, the performance of the inventive powder coating compositions was comparable to that of the comparative composition.

TABLE 8

| Composition | Flexibility[9] | Adhesion[10] | Impact Direct[11] | Impact Reverse[11] | Solvent Cure[12] | Pencil Hardness[13] |
|---|---|---|---|---|---|---|
| Example 8 (Comparative) | 1/8" | 5B | 160 in/lbs | 140 in/lbs | Cured | 2H |
| Example 5 | 1/8" | 5B | 160 in/lbs | 140 in/lbs | Cured | 2H |
| Example 6 | 1/8" | 5B | 160 in/lbs | 140 in/lbs | Cured | 2H |
| Example 7 | 1/8" | 5B | 160 in/lbs | 140 in/lbs | Cured | 2H |

[9]Measured according to ASTM D522
[10]Measured according to ASTM D3359
[11]Measured according to ASTM D2794
[12]Measured according to PCI Procedure 8, Reagent A
[13]Measured according to ASTM D3363

Examples 9-14

Powder coating compositions of the fusion bonded epoxy type were prepared using the ingredients and amounts (in parts by weight) listed in Table 9. All formulas for testing were carefully weighed and pre-mixed for 8 seconds using a Vitamix (low settings), and then processed on a 24 mm twin screw extruder. Zone 1 temperature was 100° C. and Zone 2 temperature was 100° C. The screw speed on the extruder was adjusted to attain 500 RPM and an appropriate torque of 60 to 90 Nm. The feed rate was 30, and the chiller rolls were operated at 17 degrees C. Extruder chip was ground on a mill stand for 15 seconds and then sifted thru a #140 screen (106 microns), which resulted in a powder coating composition.

TABLE 9

| | Composition | | | | | |
|---|---|---|---|---|---|---|
| Ingredients | Ex. 9 (Comp.) | Ex. 10 | Ex. 11 | Ex. 12 | Ex. 13 | Ex. 14 (Comp.) |
| Araldite ®GT-6084[15] | 325.38 | 325.38 | 325.38 | 325.38 | 325.38 | 444.13 |
| Epikure ™ P-104[16] | 17.13 | 17.13 | 17.13 | 17.13 | 17.13 | 23.38 |
| Resiflow ® P-67[17] | 5.00 | 5.00 | 5.00 | 5.00 | 5.00 | 5.00 |
| Benzoin | 2.50 | 2.50 | 2.50 | 2.50 | 2.50 | 2.50 |
| NYAD ® 400[18] | 125.00 | 112.50 | 93.75 | 62.50 | — | — |
| Tioxide ® TR60[19] | 25.00 | 25.00 | 25.00 | 25.00 | 25.00 | 25.00 |
| Organic particulate[7] | — | 12.50 | 31.25 | 62.50 | 125.00 | — |
| Total | 500 | 500 | 500 | 500 | 500 | 500 |

[15]Type 4 epoxy resin commercially available from Huntsman Advanced Materials
[16]accelerated dicyandiamide type curing agent commercially available from Hexion Inc.
[17]flow and leveling agent commercially available from Estron Chemical, Inc.
[18]400 mesh wollastonite commercially available from NYCO Minerals, Inc.
[19]rutile titanium dioxide commercially available from Huntsman International LLC.

Coated Substrates

The powder coating compositions of Examples 9-14 were applied to aluminum test panels. These were procured from Q Panel Company and consist of aluminum treated with a chromium conversion pre-coating which improves paint adhesion and resistance to underfilm corrosion. Most aluminum is given such a pretreatment prior to painting. Type AL-36 are made from alloy 3003 H14, are 0.025 in (0.64 mm) thick with overall dimensions 3"×6". The spray apparatus employed to apply the powder to the substrates was a Parker Ionics GX-131 manual spray gun set to 100 kV with the pulse power mode engaged. The coated panels were then cured by baking in an oven for 10 min at 200° C. with 3 minutes of warm up time (13 minutes total dwell time). The panels used for testing the resistance to cathodic disbondment were KTA Tator test panels for cathodic disbondment, which are mild steel panel (4"×8"×0.25") prepared using NACE SP-10 Blast method (Glass Beads). The oven used was a Precision Scientific Electric Convection Oven Model 625.

Coated aluminum panels were tested for pencil hardness, smoothness, initial gloss, color, and impact resistance. Results are set forth in Table 10.

TABLE 10

| Example | Pencil Hardness | PCI Smoothness Rating | 60° Gloss | Impact Resistance | Color L* | a* | b* |
|---|---|---|---|---|---|---|---|
| 9 | 5H | 4 | 75.6 | >40 | 80.50 | −2.19 | 12.37 |
| 10 | 5H | 3 | 75.9 | >40 | 70.61 | 1.86 | 18.52 |
| 11 | 5H | 2 | 73.7 | >60 | 61.03 | 3.24 | 20.08 |
| 12 | 5H | 2 | 73.1 | 40 | 53.51 | 5.72 | 21.37 |
| 13 | 5H | 1 | 71.3 | 40 | 44.16 | 6.85 | 20.57 |
| 14 | 5H | 4 | 100.0 | 60 | 78.78 | −2.65 | 11.19 |

Coated steel panels were tested for cathodic disbondment according to Clause 12.9 of CSA Z245.20-14. The first test was a 24 hour test. After reviewing the results, a second test round was carried out using a 30 day test. Results are set forth in Tables 11 and 12.

TABLE 11

24 Hour Test

| Example | Avg. Film Thickness (mils) | Duration (hours) | Temp. (° C.) | Volts | Individual Disbondment Radii (mm) Radial position is listed below as "clock time" | | | | | | | | Average (mm) |
| | | | | | 12:00 | 1:30 | 3:00 | 4:30 | 6:00 | 7:30 | 9:00 | 10:30 | |
|---|---|---|---|---|---|---|---|---|---|---|---|---|---|
| 9 Comparative | 14 | 24 | 65 +/− 2 | −3.5 | 2.4 | 2.7 | 2.4 | 2.3 | 2.3 | 1.8 | 1.8 | 2.3 | 2.3 |
| 10 | 19 | | | | 1.3 | 1.5 | 1.7 | 1.2 | 1.3 | 1.3 | 1.3 | 1.3 | 1.4 |
| 11 | 20 | | | | 1.5 | 1.4 | 1.4 | 1.8 | 1.4 | 2.2 | 1.7 | 1.8 | 1.7 |
| 12 | 32 | | | | 0.8 | 0.8 | 1.6 | 1.6 | 1.7 | 2.5 | 1.9 | 0.7 | 1.5 |
| 13 | 27 | | | | 2.1 | 1.7 | 1.9 | 1.2 | 1.1 | 1.1 | 2.1 | 1.9 | 1.6 |
| 14 Comparative | 30 | | | | 2.5 | 3.5 | 3.1 | 1.7 | 2.1 | 2.0 | 2.5 | 2.3 | 2.5 |

The results given in Table 11 show that all inventive compositions had lower disbondment radii than the comparative examples. No discernible trend was apparent as to the level of the Organic particulate for the inventive formulations.

TABLE 12

30 Day Test

| Example | Avg. Film Thickness (mils) | Duration (days) | Temp. (° F.) | Volts | Individual Disbondment Radii (mm) Radial position is listed below as "clock time" | | | | | | | | Average (mm) |
| | | | | | 12:00 | 1:30 | 3:00 | 4:30 | 6:00 | 7:30 | 9:00 | 10:30 | |
|---|---|---|---|---|---|---|---|---|---|---|---|---|---|
| 9 Comparative | 15 | 30 | 75 +/− 5 | −1.5 | 9.4 | 9.5 | 9.4 | 9.2 | 9.3 | 9.4 | 8.8 | 9.4 | 9.3 |
| 10 | 18 | | | | 7.4 | 7.8 | 8.1 | 8.0 | 8.1 | 8.0 | 7.6 | 7.7 | 7.9 |
| 11 | 15 | | | | 7.5 | 7.7 | 7.8 | 7.8 | 7.9 | 7.6 | 8.1 | 7.6 | 7.8 |
| 12 | 30 | | | | 5.9 | 6.3 | 6.1 | 6.1 | 6.6 | 6.3 | 6.2 | 6.2 | 6.2 |
| 13 | 40 | | | | 4.5 | 4.4 | 4.8 | 4.8 | 5.0 | 4.5 | 4.7 | 4.6 | 4.7 |
| 14 Comparative | 31 | | | | 11.0 | 10.1 | 10.2 | 10.0 | 10.0 | 9.8 | 8.7 | 8.8 | 9.9 |

The results given in Table 12, a longer duration test which should be more meaningful to discern performance differences, show a discernible trend that higher levels of Organic particulate in the powder coating formulation in improving the resistance to cathodic disbondment (smaller disbondment radii) versus the comparative examples.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A powder coating composition comprising:
   (a) a particulate film-forming resin;
   (b) an organic particulate, different from (a), comprising:
      (i) a crosslinked polymer comprising aromatic groups, biuret groups, urea groups, and carbodiimide groups; and
      (ii) a high-boiling hydrocarbon; and
   (c) a curing agent,
wherein the particulate film-forming resin comprises a carboxylic acid functional polyester resin or hydroxyl functional polyester resin.

2. A powder coating composition comprising:
   (a) a particulate film-forming resin comprising a carboxylic acid functional resin or a hydroxyl functional resin;
   (b) an organic particulate, different from (a), comprising:
      (i) a crosslinked polymer comprising aromatic groups, biuret groups, urea groups, and carbodiimide groups; and
      (ii) a high-boiling hydrocarbon; and
   (c) a curing agent comprising triglycidyl isocyanurate.

3. The powder coating composition of claim 1, wherein the organic particulate (b) is the dried product of a mixture comprising:
   (1) a residue of a polyisocyanate production process; and
   (2) a high-boiling hydrocarbon.

4. The powder coating composition of claim 3, wherein the polyisocyanate production process comprises the reaction of the corresponding amine with phosgene.

5. The powder coating composition of claim 3, wherein the polyisocyanate comprises a toluene diisocyanate.

6. The powder coating composition of claim 5, wherein the high-boiling hydrocarbon is admixed in an amount of from 2 to 50 weight %, based on the weight of the residue.

7. The powder coating composition of claim 6, wherein the high-boiling hydrocarbon comprises a bitumen.

8. The powder coating composition of claim 3, wherein the organic particulate (b) has a mean particle size of no more than 100 microns.

9. The powder coating composition of claim 3, wherein the organic particulate (b) has a specific gravity of 1.2 to 1.4.

10. The powder coating composition of claim 1, wherein the organic particulate (b) is present in the powder coating composition in an amount of at least 2% and up to 40% weight, based on the total weight of the powder coating composition.

11. The powder coating composition of claim 10, wherein the particulate film-forming resin (a) is present in the powder coating composition in an amount of 50% to 90% by weight, based on the total weight of the powder coating composition.

12. The powder coating composition of claim 11, wherein the particulate film-forming resin (a) is present in an amount of 50% to 70% by weight, based on the total weight of the powder coating composition.

13. The powder coating composition of claim 11, wherein the curing agent is present in an amount of 1 to 10% by weight, based on the total weight of the powder coating composition.

14. The powder coating composition of claim 1, further comprising at least one inorganic extender comprising talc, silicon dioxide, barium sulfate, calcium carbonate, wollastonite, calcium silicate, magnesium carbonate, micronized dolomite, or aluminum oxide.

15. The powder coating composition of claim 14, wherein the weight ratio of the organic particulate (b) to inorganic extender in the powder coating composition is 0.1:1 to 10:1.

16. The powder coating composition of claim 15, wherein the weight ratio is 1.3:1 to 3:1.

17. The powder coating composition of claim 1, wherein the organic particulate (b) is present in an amount of 2 to 25% by weight, based on the total weight of the powder coating composition.

18. The powder coating composition of claim 17, wherein the particulate film-forming resin (a) is present in an amount of 50% to 70% by weight, based on the total weight of the powder coating composition.

19. The powder coating composition of claim 17, wherein the curing agent is present in an amount of 1 to 10% by weight, based on the total weight of the powder coating composition.

20. A substrate at least partially coated with a coating deposited from the powder coating composition of claim 1.

21. An appliance, furniture or a pipeline comprising the substrate of claim 20.

22. The pipeline of claim 21, wherein the pipeline is buried in the ground or submerged in water.

\* \* \* \* \*